United States Patent
Siegemund et al.

(12)

(10) Patent No.: US 6,183,980 B1
(45) Date of Patent: Feb. 6, 2001

(54) METHOD FOR LOCATING DEFECTS IN THE CLOTTING SYSTEM

(75) Inventors: Annelie Siegemund; Thomas Siegemund, both of Mölkau (DE)

(73) Assignee: Dade Behring Marburg GmbH, Marburg (DE)

( * ) Notice: Under 35 U.S.C. 154(b), the term of this patent shall be extended for 0 days.

(21) Appl. No.: 09/461,805

(22) Filed: Dec. 16, 1999

(30) Foreign Application Priority Data

Dec. 17, 1998 (DE) .......................................... 198 58 278.1

(51) Int. Cl.[7] .............................. C12Q 1/56; C12Q 1/00
(52) U.S. Cl. .................. 435/13; 435/4; 530/380; 530/381; 436/66
(58) Field of Search ...................... 435/13, 4; 530/380, 530/381; 436/66

(56) References Cited

U.S. PATENT DOCUMENTS 5,197,017 * 3/1993 Carroll et al. .......................... 435/13
5,834,223 * 11/1998 Griffin et al. .......................... 435/13

FOREIGN PATENT DOCUMENTS

WO 91 01383 * 2/1991 (WO) .
WO 95 12127 * 5/1995 (WO) .

OTHER PUBLICATIONS

Bertina, R.M. et al., "Spectrophotometric Assays Of Prothrombin In Plasma Of Patients Using Oral Anticoagulants", Thrombois and Haemostasis, vol. 42:1296–1305 (1979).*

Corrigan, Jr., J.J. et al., "Factor II Antigen In Liver Disease And Warfarin–Induced Vitamin K Deficiency: Correlation With Coagulant Activity Using Echis Venom", American Journal of Hematology, vol. 8:249–255 (1980).*
Rosendaal, F.R. et al., "A Common Prothrombin Variant (20210 G To A) Increases The Risk Of Myocardial Infarction In Young Women", Blood, vol. 90:1747–1750 (Sep. 1, 1997).*
Brown, K. et al., "Risk Of Venous Thromboembolism Associated With A G To A Transition At Position 20210 In The 3'–Untranslated Region Of The Prothrombin Gene", British Journal Of Haematology, vol. 98:907–909 (1997).*
Rosendaal, F.R. et al., "A Common Prothrombin Variant (20210 G to A) Increases The Risk Of Myocardial Infarction In Young Women", Blood, vol. 90(5): 1747–1750, (1997).*
Bertina, Rogier, "Factor V Leiden And Other Coagulation Factor Mutations Affecting Thrombotic Risk", Clinical Chemistry, vol. 43(9): 1678–1683, (1997).*
Brown, Karen et al., "Risk Of Venous Thromboembolism Associated With a G To A Transition At Position 20210 In The 3'–Untranslated Region Of The Prothrombin Gene", British Journal of Haematology, vol. 98: 907–909, (1997).*
Poort, Swibertus R. et al., "A Common Genetic Variation In The 3'–Untranslated Region Of The Prothrombin Gene Is Associated With Elevated Plasma Prothrombin Levels And An Increase In Venous Thrombosis", Blood, vol. 88(10): 3698–3703, (1996).*

* cited by examiner

Primary Examiner—Louise N. Leary
(74) Attorney, Agent, or Firm—Finnegan, Henderson, Farabow, Garrett & Dunner, L.L.P.

(57) ABSTRACT

The present invention relates to a method for identification of defects in the clotting, fibrinolysis and complement system.

8 Claims, 3 Drawing Sheets

METHOD FOR LOCATING DEFECTS IN THE CLOTTING SYSTEM

The present invention relates to a method for identification of defects in the clotting, fibrinolysis and complement system.

Thromboses and hemorrhage are now among the most frequent causes of illness and death, especially in the industrial countries. The most well-known are cardiac infarction, apoplexy and pulmonary embolism. If thromboembolism or hemorrhage is survived, the vitality of the patient is limited in most cases, and on the one hand there are secondary symptoms, such as paralysis, post-thrombotic syndrome or organ damage, and on the other hand there are labor- and cost-intensive follow- up treatments, such as convalescence, physiotherapy and medication to improve the health situation and prevent further complications.

Great advances have been made in recent years, especially in research into the causes of thrombosis, and these include the discovery of APC resistance, lupus, anticoagulants, hyperhomocysteinemia and the prothrombin variant G20210A. Nevertheless, no cause is detectable in about 50% of all cases. The most important hemostaseological causes of hemorrhage are known, and these include the various forms of hemophilia, the von-Willebrand-Jurgens syndrome and rarer mutations of the individual clotting factors.

If such defects exist, the hemostatic equilibrium is disturbed and the ratio between pro- and anticoagulatory factors is shifted in favor of one side. Defects which result in an increased secretion of procoagulatory factors, for example the prothrombin variant G20210A, deficient release of inhibitors, such as with protein C, protein S or AT III deficiency, or the prevention of inhibition by modified receptors, in its best-known form resistance to the active form of protein C (APC resistance: Bertina R M, Clin Chem; 43(9): 1678–83), usually lead to thromboses. To these are added defects in the fibrinolysis system which reduce the breakdown of clots formed.

It is the task of the laboratory to identify such defects so that the doctor performing the treatment can estimate the individual risk of the patient and react to this. Various methods of diagnosis are employed here: global tests determine the interaction of several components of the clotting system. The prothrombin time (PT) determines the state of the exogenous clotting system and the partial thromboplastin time (aPTT) determines the state of the endogenous clotting system. Modified global tests are furthermore employed in the analysis of the protein C system and in the diagnosis of lupus anticoagulants. In contrast to these there are individual tests, each of which determine only an individual component and allow both qualitative and quantitative analysis. Modified individual tests are employed in the question of acquired inhibiting bodies. In spite of the diverse methods which can be chosen, an accurate diagnosis is often not possible: the boundaries between a "positive" and "negative" finding are not clear, or medicaments, such as, for example, anticoagulants, have a persistent influence on the test result.

DNA analysis provides unambiguous diagnoses of congenital defects. This is suitable above all for defects which are based on an individual mutation, such as factor V condition (a form of APC resistance) or the prothrombin variant G20210A. If heterogeneous defects exist, genetic analysis is also made extremely difficult. Needless to say, other problems arise in connection with DNA analysis. Only few laboratories are capable of conducting such an investigation, and there are also the high costs associated with it.

It is therefore an aim to select the patient group before the DNA analysis in order to save work and costs. The best known example here is resistance to protein C. There are various tests for investigating for APC resistance. If a positive finding is obtained, a genetic analysis can be carried out to discover whether the very frequent form of factor V condition exists. Such a separation between "positive" and "negative" also has a second decisive advantage. If an unknown defect is to be searched for, patient groups could be separated and selected out as "potentially positive" and analyzed by gene sequencing. To date, these groups have been selected according to the case history.

The prothrombin variant G20210A is a very good example of these problems. This point mutation is associated with increased prothrombin levels which lead to an increased risk of thrombosis (Poortn, Blood 1996; 88 (10): 3698–703). Publications indicate an increased risk of cardiac infarctions (Rosendahl, Blood 1997; 90(5) 1747–50) and venous thromboses (Brown, Br. J. Haematol; 98(4): 907–9). However, it has also been possible to demonstrate that discrimination between mutation carrier and the wild type is not possible with the aid of the prothrombin level, since the two groups cannot be separated (Poortn, Blood 1996; 88(10): 3698–703; see also our own results). Patients under oral anticoagulation had to be excluded.

Surprisingly, we found a possibility of achieving a very good separation between carriers of the mutation and carriers of the wild type gene. This was to be achieved by relating the result of an individual test to an associated search test. The tests which belong together are known to the expert. The relationship in which the individual test and search test can be placed is preferably the ratio. The sensitivity, specificity and cut-off are parameters which are important for the discrimination. As can be seen from the examples, the specificity can be increased at the expense of the sensitivity by varying the cut-off. A lower sensitivity is preferably taken, in order to increase the specificity. Preferably, a sensitivity of a maximum of 100%, particularly preferably a sensitivity of 95–100%, especially preferably a sensitivity of 80–95% is taken to increase the specificity. On the basis of the technical doctrine of the present invention, the expert can set the desired ratio of sensitivity and specificity by determination of a suitable cut-off value by simple experiments.

Acquired diseases can thus also be diagnosed, since these likewise cause hypo- or hypercoagulatory states which are distinguished by only a slight, in itself often insignificant change in the activity of the parameter affected.

ratio=factor II concentration [% of N.]/prothrombin time (PT) [% of N.]

Figure 3:
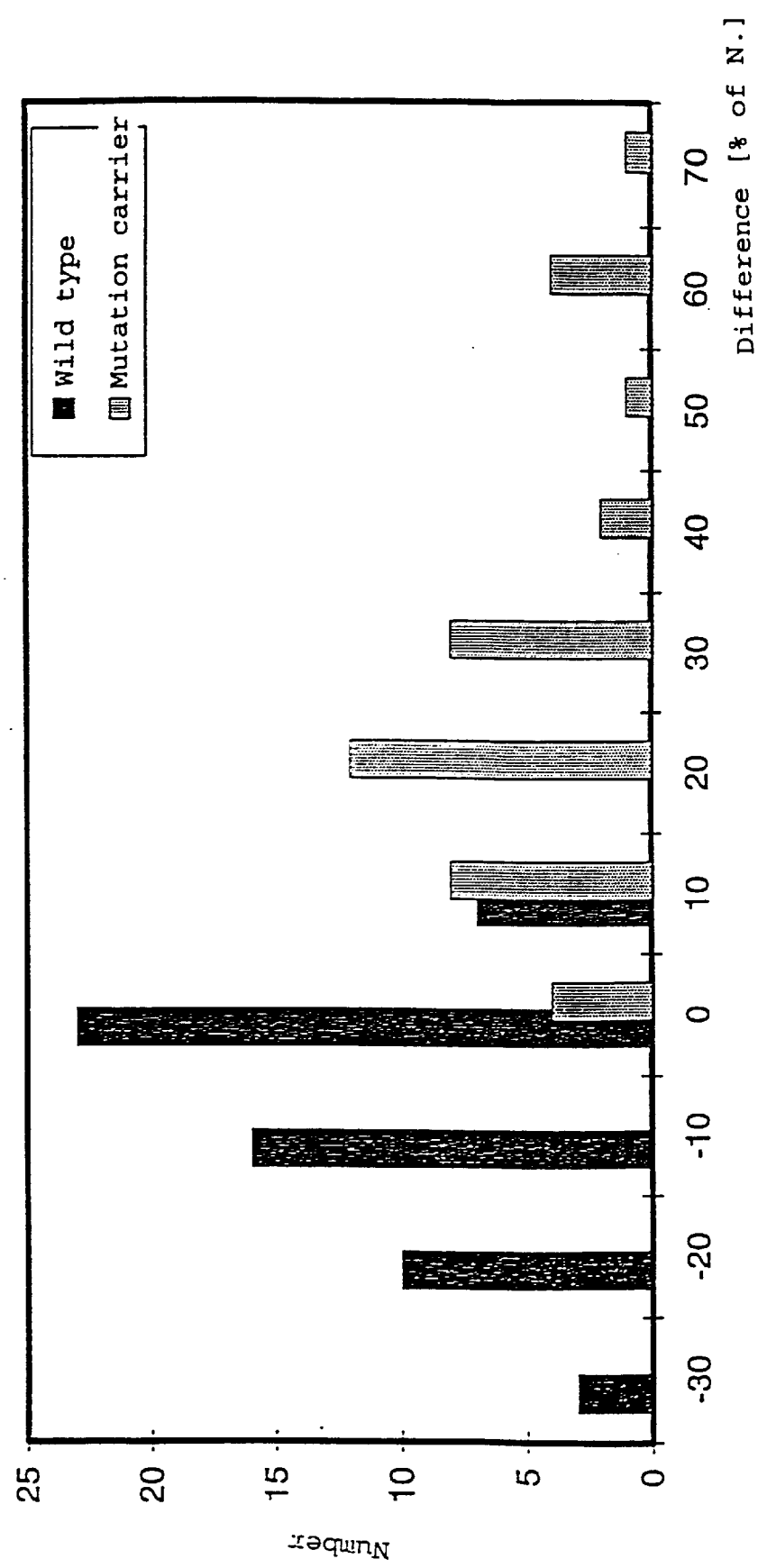

FIG. 3 shows the determination according to the invention of mutation carriers on the same group of samples.

The following examples are intended to illustrate the invention but in no way limit the claims.

Example 1

The prothrombin variant G20210A is to be given as an example.

The data available here were determined as follows: 46 blood donors and 53 thrombosis patients were divided into the groups of mutation carriers (40) and wild types (59) with the aid of a PCR from EDTA blood (DNA isolation and amplification, allele-specific hybridization with labeled probes in microtiter strips; Medizinische Diagnostische Produkt GmbH) From citrate blood, the factor II concentration (Factor II-Testkit, Dade Behring Marburg GmbH; ACL, Instrumentation Laboratory) and the prothrombin time (Immunoplastin IS, Immuno GmbH, BCT Dade Behring Marburg GmbH) were determined for the two groups.

Figure 1:
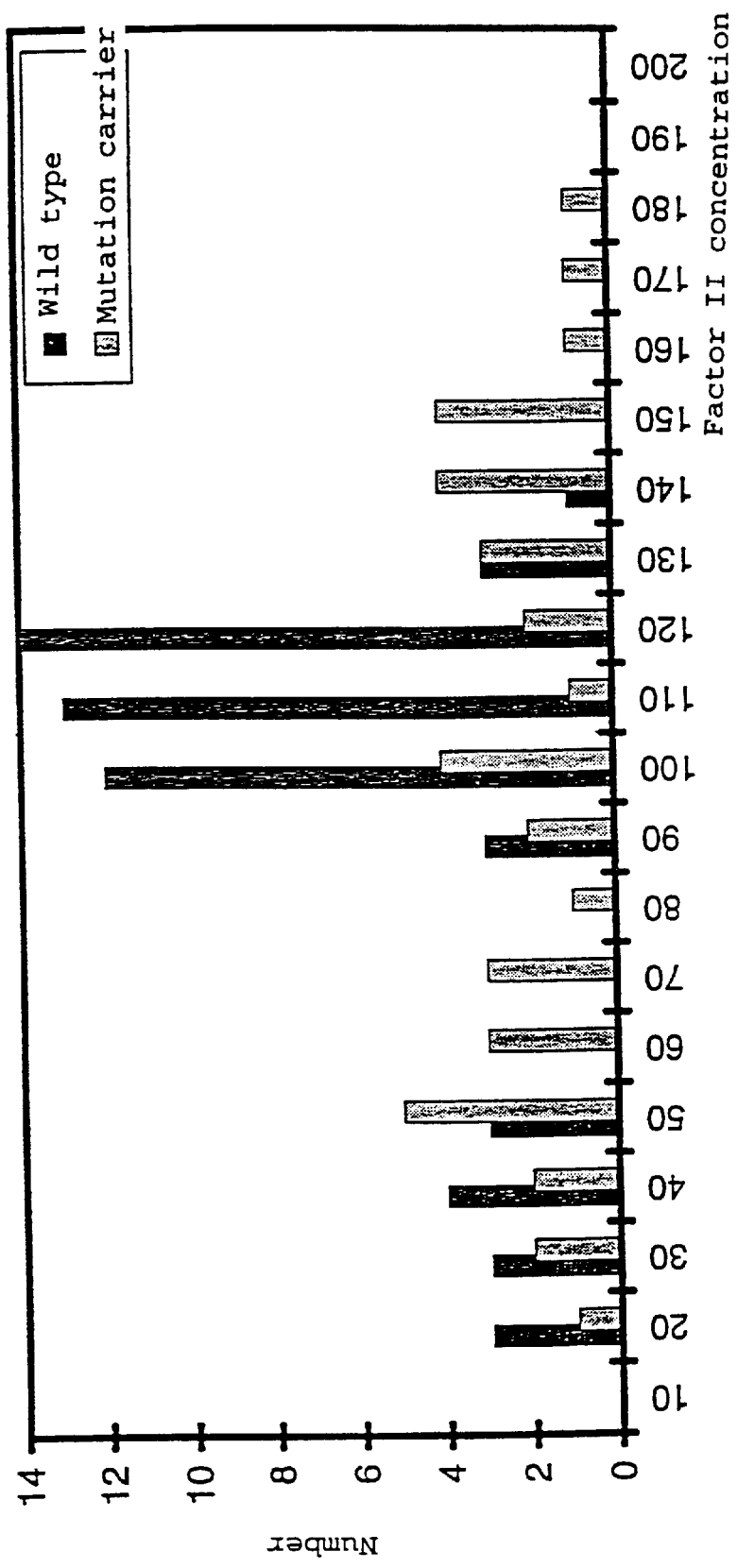
FIG. 1: shows the determination of mutation carriers by the method according to the prior art (determination of the factor II concentration) on 46 blood donors (wild type) and 54 thrombosis patients.

The distribution of the factor II concentration is shown in FIG. 1 (method according to the prior art).

Figure 2:
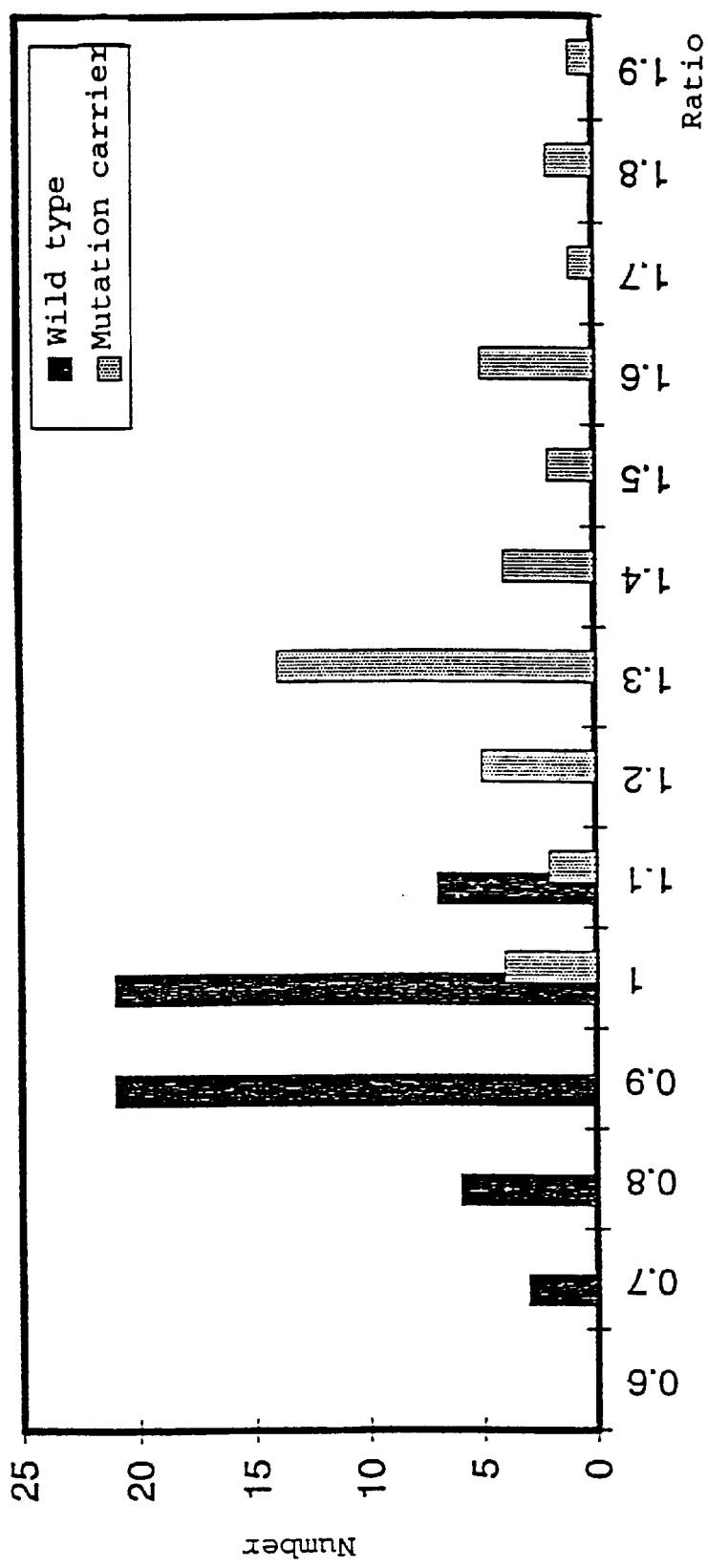
FIG. 2: shows the determination according to the invention of mutation carriers on the same group of samples (ratio method) according to the following formula.

The distribution of the ratio according to the following formula is shown in FIG. 2 (method according to the invention):

ratio=factor II concentration [% of N.]/prothrombin time (PT) [% of N.]

To demonstrate the advantages of the method according to the invention, a statistical evaluation of the two methods follows. In the first step, sensitivity values of 100%, 95% and 90% are the condition, and the cut-off and specificity are in each case determined for the two procedures:

|  | Discrimination according to | |
|---|---|---|
|  | Factor II concentration (prior art) | Ratio (method according to the invention) |
| Sensitivity | 100% | 100% |
| Cut-off | 13% of N. | 0.95 |
| Specificity | 0% | 64% |
| Sensitivity | 95% | 95% |
| Cut-off | 29% of N. | 0.99 |
| Specificity | 10% | 83% |
| Sensitivity | 90% | 90% |
| Cut-off | 33% of N. | 1.02 |
| Specificity | 10% | 92% |

In the second step, a specificity of 100% is taken:

|  | Discrimination according to | |
|---|---|---|
|  | Factor II concentration (prior art) | Ratio (method according to the invention) |
| Specificity | 100% | 100% |
| Cut-off | 132% of N. | 1.07 |
| Sensitivity | 28% | 85% |

The advantages of the method according to the invention can be clearly seen from the values obtained.

Example 2

The same conditions as in Example 1 apply. The distribution after obtaining the difference is shown in FIG. 3:

Difference [% of N.]=prothrombin time (PT) [% of N.]factor II concentration [% of N.]

To demonstrate the advantages of the method according to the invention, a statistical evaluation of the two methods follows. In the first step, sensitivity values of 100%, 95% and 90% are the condition, and the cut-off and specificity are in each case determined for the two procedures:

|  | Discrimination according to | |
|---|---|---|
|  | Factor II concentration (prior art) | Difference (method according to the invention) |
| Sensitivity | 100% | 100% |
| Cut-off | 13% of N. | −6% of N. |
| Specificity | 0% | 63% |
| Sensitivity | 95% | 95% |
| Cut-off | 29% of N. | −1% of N. |
| Specificity | 10% | 80% |
| Sensitivity | 90% | 90% |
| Cut-off | 33% of N. | 2% of N. |
| Specificity | 10% | 93% |

In the second step, a specificity of 100% is taken:

|  | Discrimination according to | |
|---|---|---|
|  | Factor II concentration (prior art) | Difference (method according to the invention) |
| Specificity | 100% | 100% |
| Cut-off | 132% of N. | −6% of N. |
| Sensitivity | 28% | 78% |

The advantages of the method according to the invention can be clearly seen from the values obtained.

What is claimed is:

1. A method for detection of defects of a selected analytical parameter of a multistage, multifactorial biochemical reaction system which includes the following steps:
   (a) determination of the analytical parameter,
   (b) selection of a global search test and
   (c) establishment of a correlation of the values measured for (a) and (b).

2. The method as claimed in claim 1, wherein the multistage, multifactorial biochemical reaction system is the fibrinolysis system.

3. The method as claimed in claim 1, wherein the multistage, multifactorial biochemical reaction system is the clotting system.

4. The method as claimed in claim 1, wherein the multistage, multifactorial biochemical reaction system is the complement system.

5. The method as claimed in one of claims 1 to 4, wherein the correlation is chosen from the group consisting of: ratio, product, difference, and total.

6. The method as claimed in claim 1, wherein the analytical parameter is chosen from the group consisting of: factor II, V, VII, X, XI and XII.

7. A method claimed in claim 1, wherein the global search test (b) is chosen from the group consisting of: prothrombin time and partial prothrombin time.

8. The method as claimed in claim 1, wherein the discrimination between carriers of a mutated gene and carriers of a wild-type gene is achieved by specifying a suitable cut-off.

* * * * *